(12) United States Patent
Goldstein

(10) Patent No.: US 9,320,420 B2
(45) Date of Patent: Apr. 26, 2016

(54) VIDEO LARYNGOSCOPE PROVIDING SUCTION

(76) Inventor: Rachel A. Goldstein, Chicago, IL (US)

(*) Notice: Subject to any disclaimer, the term of this patent is extended or adjusted under 35 U.S.C. 154(b) by 0 days.

(21) Appl. No.: 12/908,582

(22) Filed: Oct. 20, 2010

(65) Prior Publication Data

US 2011/0092773 A1    Apr. 21, 2011

Related U.S. Application Data

(60) Provisional application No. 61/253,522, filed on Oct. 21, 2009.

(51) Int. Cl.
*A61B 1/267* (2006.01)
*A61B 1/015* (2006.01)

(52) U.S. Cl.
CPC ............... *A61B 1/267* (2013.01); *A61B 1/015* (2013.01)

(58) Field of Classification Search
CPC ................................ A61B 17/02; A61B 1/267
USPC ............... 600/184–249; 128/200.26
See application file for complete search history.

(56) References Cited

U.S. PATENT DOCUMENTS

| 4,126,127 | A | * | 11/1978 | May | 600/187 |
| 4,880,015 | A | * | 11/1989 | Nierman | 600/564 |
| 7,608,040 | B1 | * | 10/2009 | Dunst | 600/187 |
| 2002/0022769 | A1 | * | 2/2002 | Smith et al. | 600/188 |
| 2005/0043590 | A1 | * | 2/2005 | Mazzei et al. | 600/188 |
| 2007/0112257 | A1 | * | 5/2007 | Hensler | 600/199 |

FOREIGN PATENT DOCUMENTS

IL    WO 2009/019703    *    2/2009    ............ A61B 1/04

* cited by examiner

*Primary Examiner* — Matthew Lawson
(74) *Attorney, Agent, or Firm* — Avery N. Goldstein; Blue Filament Law

(57) ABSTRACT

A video laryngoscope is provided that includes a body having a handle portion and a blade portion. The blade portion terminates in a tip and defines at least one aperture formed proximal to the tip. The blade portion is dimensioned for oral insertion into a subject buccal cavity. A fiber optic light source terminates within the blade portion and upon light source activation illuminates an area including the tip. A video system is coupled to the body and relays imagery of the tip and surrounding area to a video monitor. A channel extending through the body provides fluid communication to the aperture and an external source of suction. As a result, an operator is capable of visualizing debris and/or obstructions in a subject airway and is able to observe and guide the scope for suction removal.

13 Claims, 1 Drawing Sheet

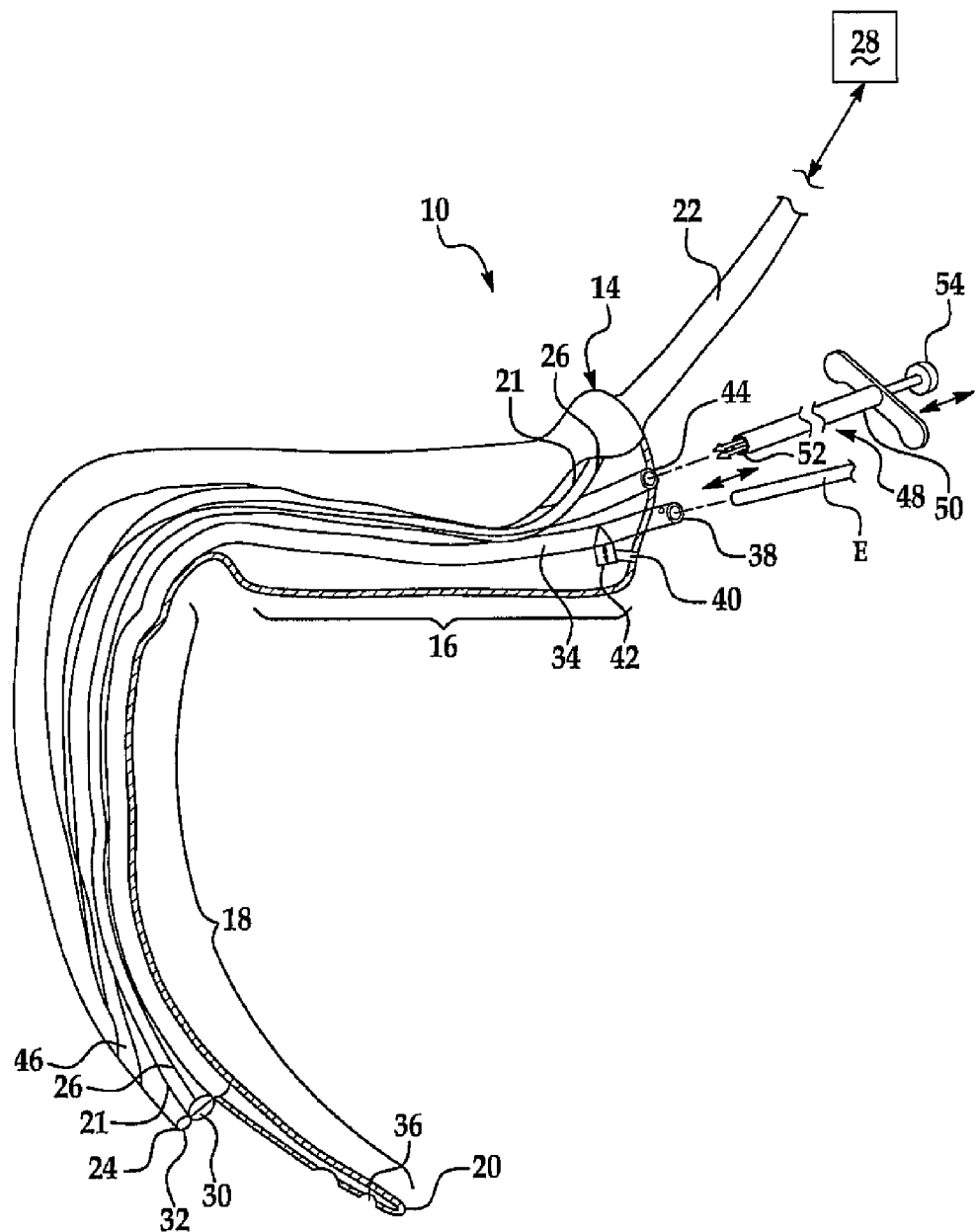

VIDEO LARYNGOSCOPE PROVIDING SUCTION

CROSS-REFERENCE TO RELATED APPLICATIONS

This application claims priority of U.S. Provisional Patent Application Ser. No. 61/253,522 filed Oct. 21, 2009, which is incorporated herein by reference.

FIELD OF THE INVENTION

The present invention in general relates to a laryngoscope and in particular to a video laryngoscope having suction capabilities to clear the airway during blade insertion.

BACKGROUND OF THE INVENTION

A laryngoscope is regularly used in an emergency room setting to examine and intubate an individual having a compromised airway or undergoing a surgical procedure. Prior to the integration of a video system into a laryngoscope, a physician attempting to intubate an individual had to rely on tactile sensation to find a path of least resistance in which to insert intubation tubing. Incorporation of a video system into a laryngoscope provides visual feedback as to the optimal path of laryngoscope blade insertion for intubation and also serves to provide visual inspection of airway condition. Unfortunately, a laryngoscope video system is compromised by blood, fulminate fluid, debris, or damage to the airway; and in such situations, a physician must again resort to tactile feel in order to intubate. The inability to intubate can result in damage to the larynx as well as the requirement that an emergency tracheotomy be performed. In many instances when a visual system of a video laryngoscope is compromised by blood, fulminate fluid, or other material in the airway, the ability to clearly direct a laryngoscope is restored currently by simultaneously guiding a suction tube into the throat of an individual. However, the simultaneous manipulation of a suction tube with a laryngoscope is complicated by the flexible nature of the suction tube and the difficulty in orchestrating coordinated movement between the laryngoscope and the suction tube.

Thus, there exists a need for a video laryngoscope incorporating a suction capability into the laryngoscope blade.

SUMMARY OF THE INVENTION

A video laryngoscope is provided that includes a body having a handle portion and a blade portion. The blade portion terminates in a tip and defines at least one aperture formed proximal to the tip. The blade portion is dimensioned for oral insertion into a subject buccal cavity. A fiber optic light source terminates within the blade portion and upon light source activation illuminates an area including the tip. A video system is coupled to the body and relays imagery of the tip and surrounding area to a video monitor. A channel extending through the body provides fluid communication to the aperture and an external source of suction. As a result, an operator is capable of visualizing debris and/or obstructions in a subject airway and is able to observe and guide the scope for suction removal.

BRIEF DESCRIPTION OF THE DRAWINGS

FIG. 1 is a cross-sectional view of an inventive laryngoscope.

DESCRIPTION OF THE INVENTION

The present invention has utility as a laryngoscope for the visualization of a human larynx. The present invention is further detailed with respect to FIG. 1 in which an inventive laryngoscope is shown generally at 10. The laryngoscope is defined by a body 14 having a handle portion 16 and a blade portion 18. The blade portion 18 terminates in a tip 20. The blade portion 18 is dimensioned for oral insertion into the buccal cavity and throat of a subject. It is appreciated that the dimensions of a blade portion 18 are readily modified to accommodate various species such as humans and other non-human mammals such as dogs, cats, horses, cows, sheep, and pigs. Additionally, it is appreciated that a blade portion 18 is further dimensioned to accommodate individuals of different sizes within a species ranging from pediatric through adult through morbidly obese. A body 14 is readily formed from medical grade synthetic polymers. Preferably, the body 14 is formed from two complementary portions that roughly join around the boundaries of body 14 as depicted in FIG. 1. A fiber optic light source 21 extends between a cable 22 and a terminus 24 proximal to tip 20. Transmission of illumination through the cable 22 via the terminus 24 serves to illuminate the tip 20 and the surrounding region. A video system fiber optic 26 collects imagery of the tip 20 and a surrounding spatial region from a fiber optic terminating in the vicinity of the terminus 24 and extending to the cable 22. The cable 22 conveys imagery of the tip 20 and surrounding spatial region to a conventional video system and display 28. Optionally, a lens 30 is provided at terminus 24 to modify focus or visual field collected by the video system fiber 26. Illumination via fiber optic 21 is also optionally projected outward through the lens 30 or a secondary lens 32 so provided. A channel 34 provides fluid communication through the body 14 to at least one aperture 36 situated proximal to tip 20. The channel 34 upon being coupled to a vacuum source draws mucus, blood, fulminate fluid, small foreign bodies, or a combination thereof through the apertures 36 and into channel 34 to improve the visual acuity of the tip 20 and surrounding anatomy upon insertion into the laryngeal cavity of a subject. The channel 34 optionally terminates in a fitting 38 complementary to engage an external suction source E. The channel 34 having a fitting 38 adapted to engage an external suction E also optionally includes a bore hole 40 in the handle portion 16 that, upon being covered by a finger of a user, selectively draws a suction at the at least one aperture 36 thereby creating fluid communication between the external suction line E via the channel 34. Optionally, the bore hole 40 is in mechanical communication with an airtight valve 42 such as a needle valve. In an alternative embodiment, the channel 34 is sized to accommodate a conventional external suction tube into the volume thereof so as to generate a suction at aperture 36. In such an instance, an external suction trigger controls the degree of vacuum pull at aperture 36.

Optionally, inventive laryngoscope 10 has a bore 44 extending from the handle portion 16 through the blade portion 18 and terminating in an opening 46. The bore 44 is sized to receive a flexible pickup 48 having a springed sheath 50 and retractable forceps 52 in mechanical communication with a plunger 54. Upon the flexible pickup 48 extending beyond the opening 46, and upon depression of the plunger 54, the forceps 52 extend from the sheath 50 and into the optical field of the video system 26 to allow a physician to grasp and remove foreign objects with reliance on the laryngoscope video system and the flexible pickup 48.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A video laryngoscope comprising:
 a body having a handle portion and a curved blade portion terminating in a tip having a distal end, the blade portion defining at least one aperture formed proximal to the tip, the curved blade portion dimensioned for oral insertion into a buccal cavity of a subject;
 a fiber optic light source terminating within the curved blade portion and upon activation directly illuminates an area including the distal end of the tip and the at least one aperture, said fiber optic light source is recessed behind the at least one aperture;
 a video system coupled to said body and relaying imagery of the tip to a video monitor; an external suction tube; and
 a channel extending through said body providing fluid communication to the at least one aperture and an external source of suction, said channel sized to accommodate said external suction tube insertion into said channel so as to generate a suction at the at least one aperture, the at least one aperture having an aperture area smaller than a cross section of said channel such that said external suction tube is confined within said channel.

2. The laryngoscope of claim 1 wherein said channel further comprises a fitting engaging an external suction line as said suction source.

3. The laryngoscope of claim 2 further comprising a bore hole for selectively providing fluid communication between said external suction line and the at least one aperture upon closure of the bore hole.

4. The laryngoscope of claim 3 further comprising a trigger and a valve located on a distal end of the handle portion relative to the tip and intermediate between the bore hole and said external suction line.

5. The laryngoscope of claim 3 further comprising an external suction trigger that controls a degree of vacuum pull at the at least one aperture.

6. The laryngoscope of claim 1 wherein said channel terminates in the handle portion.

7. The laryngoscope of claim 1 wherein the at least one aperture is a plurality of apertures intermediate between the tip and a terminus of said fiber optic light source.

8. The laryngoscope of claim 1 further comprising a bore extending through said body and terminating at an opening in the curved blade portion, and a flexible pickup adapted to extend through said bore and the opening and into the area illuminated by said fiber optic light source and imaged by said video system.

9. The laryngoscope of claim 8 wherein said flexible pickup has forceps that extend from a sheath.

10. A process of clearing a subject airway comprising:
 inserting a video laryngoscope of claim 1;
 holding the handle portion with one hand; and
 engaging the external source of suction to evacuate the subject airway with the one hand.

11. The process of claim 10 further comprising watching the video monitor during the engagement of the external source of suction.

12. The process of claim 10 wherein the engagement of the external source of suction is depression of an external suction trigger.

13. The process of claim 10 further comprising extending a flexible pickup through the video laryngoscope and into the subject airway to grab debris from the subject airway.

* * * * *